(12) United States Patent
Kecht et al.

(10) Patent No.: US 9,327,542 B2
(45) Date of Patent: May 3, 2016

(54) VALUE DOCUMENT, METHOD FOR CHECKING THE PRESENCE OF SAME AND VALUE DOCUMENT SYSTEM

(71) Applicant: GIESECKE & DEVRIENT GMBH, Munich (DE)

(72) Inventors: Johann Kecht, Munich (DE); Wolfgang Rauscher, Parkstetten (DE); Stephan Steinlein, Munich (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 0 days.

(21) Appl. No.: 14/410,174

(22) PCT Filed: Jun. 28, 2013

(86) PCT No.: PCT/EP2013/001905
§ 371 (c)(1),
(2) Date: Dec. 22, 2014

(87) PCT Pub. No.: WO2014/005686
PCT Pub. Date: Jan. 9, 2014

(65) Prior Publication Data
US 2015/0328915 A1    Nov. 19, 2015

(30) Foreign Application Priority Data

Jul. 3, 2012   (DE) .......................... 10 2012 013 244

(51) Int. Cl.
*G01N 21/64*   (2006.01)
*B42D 25/29*   (2014.01)
(Continued)

(52) U.S. Cl.
CPC ............... *B42D 25/30* (2014.10); *B42D 25/29* (2014.10); *D21H 21/48* (2013.01); *G01N 21/64* (2013.01);
(Continued)

(58) Field of Classification Search
CPC .... B42D 2033/20; B42D 25/29; B42D 25/30; B42D 25/382; D21H 21/48; G01N 21/64; G07D 7/00; G07D 7/122
See application file for complete search history.

(56) References Cited

U.S. PATENT DOCUMENTS

| 4,863,783 A | 9/1989 | Milton |
| 2008/0163994 A1 | 7/2008 | Hoppe et al. |
| 2009/0258200 A1 | 10/2009 | Scholz et al. |

FOREIGN PATENT DOCUMENTS

| DE | 102004027416 A1 | 12/2005 |
| DE | 102005019980 A1 | 11/2006 |

(Continued)

OTHER PUBLICATIONS

International Search Report from PCT Application No. PCT/EP2013/001905, Feb. 10, 2014.

(Continued)

*Primary Examiner* — Mark R Gaworecki
(74) *Attorney, Agent, or Firm* — Workman Nydegger

(57) ABSTRACT

The invention relates to a value document having luminescent, particulate agglomerates which respectively include at least two different, luminescent, solid homogeneous phases emitting at a first and a second emission wavelength, respectively, wherein upon an evaluation of measurement values that are obtainable by a measurement of the first luminescence intensity at the first emission wavelength and of the second luminescence intensity at the second emission wavelength, said measurement being location-specific and carried out at different locations, a statistical correlation is present between the first luminescence intensities and the second luminescence intensities.

9 Claims, 6 Drawing Sheets

Signal A    Signal B    Signal A    Signal B    Signal A    Signal B (51) Int. Cl.
  *B42D 25/30* (2014.01)
  *G07D 7/00* (2006.01)
  *G07D 7/12* (2006.01)
  *D21H 21/48* (2006.01)
  *B42D 25/382* (2014.01)

(52) U.S. Cl.
  CPC .............. *G07D 7/00* (2013.01); *G07D 7/122* (2013.01); *B42D 25/382* (2014.10); *B42D 2033/20* (2013.01)

(56) References Cited

FOREIGN PATENT DOCUMENTS

| DE | 102005047609 A1 | 4/2007 |
|----|-----------------|--------|
| EP | 1826730 A2 | 8/2007 |
| WO | 2006053685 A2 | 5/2006 |
| WO | 2006072380 A2 | 7/2006 |

OTHER PUBLICATIONS

International Preliminary Report on Patentability from PCT Application No. PCT/EP2013/001905, Jan. 6, 2015.
"Correlation and dependence", Wikipedia, 10 pages. Retrieved from the Internet Apr. 13, 2015. http://en.wikipedia.org/wiki/Correlation_and_dependence.
"Spearman's rank correlation coefficient", Wikipedia, 8 pages. Retrieved from the Internet Apr. 13, 2015. http://en.wikipedia.org/wiki/Spearman%27s_rank_correlation_coefficient.
"Statistik: Korrelationsanalyse", Wikipedia, 14 pages. Retrieved from the Internet Apr. 13, 2015. http://de.wikibooks.org/wiki/Statistik:_Korrelationsanalyse.
"Rangkorrelationskoeffizient", Wikipedia, 6 pages. Retrieved from the Internet Apr. 13, 2015. http://de.wikipedia.org/wiki/Rangkorrelationskoeffizient.

1) Raw Data   2) Standardization   3) Rotation about 45°   4) Quantiles

VALUE DOCUMENT, METHOD FOR CHECKING THE PRESENCE OF SAME AND VALUE DOCUMENT SYSTEM

BACKGROUND

This invention relates to a value document such as a bank note, to a method for checking the presence of the same, and to a value-document system.

The authentication of value documents by means of luminescent substances has been known for some time. Use is preferably made of host lattices doped with rare earth metals, with the absorption ranges and emission regions being variable within a wide range through a suitable coordination of rare earth metal and host lattice. The employment of magnetic and electrically conductive materials for authentication is also per se known. Magnetism, electrical conductivity and luminescence emission are detectable by machine using commercially available measurement devices, while luminescence is also detectable visually when emission in the visible range is of sufficient intensity.

The problem of the authentication features of value documents being forged is practically as old as the authentication of the value documents. Anti-forgery security can be increased for example by employing not only one feature substance, but a plurality of feature substances in combination, for example a luminescent substance and a magnetic substance, or a luminescent substance and a substance influencing the luminescence properties. DE 10 2005 047 609 A1 describes feature substances for authentication of value documents that contain a luminescent substance and at least one further substance that is preferably magnetic or electrically conductive. The luminescent substance is present in particulate form and is surrounded by a shell formed from nanoparticles. The properties of the feature substance result from the interaction of the luminescence emission properties of the luminescent substance and the properties of the nanoparticles.

SUMMARY

Starting out from this prior art, the present invention is based on the object of providing a value document that is improved in terms of anti-forgery security, and a method for checking the presence of the same.

SUMMARY OF THE INVENTION

A first aspect of the invention relates to a value document having luminescent, particulate agglomerates which respectively include at least two different, luminescent, solid homogeneous phases emitting at a first and a second emission wavelength, respectively, wherein upon an evaluation of measurement values that are obtainable by a measurement of the first luminescence intensity at the first emission wavelength and of the second luminescence intensity at the second emission wavelength, said measurement being location-specific and carried out at different locations, a statistical correlation is present between the first luminescence intensities and the second luminescence intensities.

It is preferable that the luminescence intensities used for the evaluation are, respectively, corrected measurement values converted by means of an algorithm.

Furthermore, it is preferable that the agglomerates are chosen from the group consisting of core-shell particles, pigment agglomerates, encapsulated pigment agglomerates and pigments encased by nanopigments.

Further, it is preferable that the particulate agglomerates have a grain size D99 in a range of 1 micrometer to 30 micrometers, further preferably in a range of 5 micrometers to 20 micrometers, yet further preferably in a range of 10 micrometers to 20 micrometers, and particularly preferably in a range of 15 micrometers to 20 micrometers.

In addition or as an alternative to the hereinabove described values of the grain size D99, it is further preferable that the particulate agglomerates have a grain size D50 in a range of 1 micrometer to 30 micrometers, further preferably in a range of 5 micrometers to 20 micrometers, and particularly preferably in a range of 7.5 micrometers to 20 micrometers.

D99 and D50 designate that 99% and 50% of the particles of a grain-size distribution have grain sizes that are smaller than or equal to this value.

A second aspect of the invention relates to a method for checking the presence of a value document according to the first aspect of the invention, said method comprising the following steps:

a) exciting the luminescent substances to emission;

b) capturing measurement values in a location-resolved and wavelength-selective manner for the radiation emitted by the luminescent substances, there being produced for each of the first and the second emission wavelength measurement-value pairs involving emission wavelength and location, to thereby obtain first luminescence intensities at the first emission wavelength and second luminescence intensities at the second emission wavelength;

c) checking whether a statistical correlation is present between the first luminescence intensities and the second luminescence intensities.

A third aspect of the invention relates to a value-document system having at least first value documents and second value documents, wherein the first value documents are respectively chosen according to the first aspect of the invention, and the first value documents are distinguishable from the second value documents by the statistical correlation of their luminescence intensities.

As a value-document system there can be chosen e.g. one having a plurality of types of bank notes of different denomination.

According to a preferred variant, the value-document system can be so adapted that the second value documents have no statistical correlation.

According to a further, preferred variant, the value-document system comprises first value documents, second value documents, third value documents and fourth value documents, of which the third value documents and the fourth value documents are only optional, namely:

a) first value documents respectively having a luminescent mixture consisting of luminescent, particulate agglomerates (A+B) and luminescent particles C, wherein the particulate agglomerates (A+B) respectively include two different, luminescent, solid homogeneous phases A and B emitting at a first and a second emission wavelength, respectively, and the luminescent particles C respectively consist of a solid homogeneous phase C emitting at a third emission wavelength, and upon an evaluation of measurement values that are obtainable by a measurement of the first luminescence intensity at the first emission wavelength, of the second luminescence intensity at the second emission wavelength and of the third luminescence intensity at the third emission wavelength, said measurement being location-specific and carried out at different locations, a statistical correlation is present only between the first luminescence intensities and the second luminescence intensities;

b) second value documents respectively having a luminescent mixture consisting of luminescent, particulate agglomerates (B+C) and luminescent particles A, wherein the particulate agglomerates (B+C) respectively include the two different, luminescent, solid homogeneous phases B and C emitting at the second and the third emission wavelength, respectively, and the luminescent particles A respectively consist of the solid homogeneous phase A emitting at the first emission wavelength, and upon an evaluation of measurement values that are obtainable by a measurement of the first luminescence intensity at the first emission wavelength, of the second luminescence intensity at the second emission wavelength and of the third luminescence intensity at the third emission wavelength, said measurement being location-specific and carried out at different locations, a statistical correlation is present only between the second luminescence intensities and the third luminescence intensities;

optionally c) third value documents respectively having a luminescent mixture consisting of luminescent, particulate agglomerates (A+C) and luminescent particles B, wherein the particulate agglomerates (A+C) respectively include the two different, luminescent, solid homogeneous phases A and C emitting at the first and the third emission wavelength, respectively, and the luminescent particles B respectively consist of the solid homogeneous phase B emitting at the second emission wavelength, and upon an evaluation of measurement values that are obtainable by a measurement of the first luminescence intensity at the first emission wavelength, of the second luminescence intensity at the second emission wavelength and of the third luminescence intensity at the third emission wavelength, said measurement being location-specific and carried out at different locations, a statistical correlation is present only between the first luminescence intensities and the third luminescence intensities; and optionally d) fourth value documents respectively having luminescent, particulate agglomerates (A+B+C), wherein the particulate agglomerates (A+B+C) respectively include the three different, luminescent, solid homogeneous phases A, B and C emitting at the first, the second and the third emission wavelength, respectively, and upon an evaluation of measurement values that are obtainable by a measurement of the first luminescence intensity at the first emission wavelength, of the second luminescence intensity at the second emission wavelength and of the third luminescence intensity at the third emission wavelength, said measurement being location-specific and carried out at different locations, a statistical correlation is present between the first luminescence intensities, the second luminescence intensities and the third luminescence intensities.

DETAILED DESCRIPTION OF THE INVENTION

Value documents within the framework of this invention are objects such as bank notes, checks, shares, value stamps, identity cards, passports, credit cards, deeds and other documents, labels, seals, and objects to be authenticated such as for example CDs, packages and the like. The preferred area of application is bank notes which are in particular based on a paper substrate.

Luminescent substances are standardly used for safeguarding bank notes. In the case of a luminescent authentication feature which is e.g. incorporated in the paper of a bank note at different places, the luminescence signals of the feature are naturally subject to certain fluctuations at the different places. The present invention is based on the finding that a targeted production of mixed, particulate agglomerates of two different luminescent substances results in the effect of a statistical correlation of the intensity fluctuations of the luminescence signals of the two substances. In this manner it is possible to distinguish the samples according to the invention by evaluating the agglomerate-induced signal correlation of non-correlating authentication features. Evaluation of the agglomerate-induced signal correlation can be performed e.g. by means of a computing unit in a sensor. Non-correlating authentication features are in particular the mixtures of individual, untreated powdery luminescent substances.

The use of the above effect leads to an increase of anti-forgery security because non-correlating feature signals can be recognized as "false" in spite of the same band position and intensity. Furthermore, the number of the possible encodings can be increased. There can thus be additionally generated from an encoding containing the individual luminescent feature substances A, B and C, by means of a targeted particulate agglomeration of two and three of the luminescent feature substances, respectively, the four distinguishable variants (A+B),C/A,(B+C)/(A+C),B/(A+B+C), where the signals of the substances within a bracket respectively correlate with each other.

The particulate agglomerates according to the invention have at least two different luminescent substances which are excitable to luminescence emission, preferably phosphorescence emission, independently of each other by radiation in the infrared and/or visible and/or ultraviolet region. The adhesion of the two luminescent substances present in the form of solid homogeneous phases must be strong enough so that during storage and processing there is no separation of the two luminescent substances, at least not to an extent that will disturb the manufacture of security features.

The particulate agglomerates according to the invention may involve in particular core-shell particles, pigment agglomerates, encapsulated pigment agglomerates or pigments encased by nanopigments. Pigment agglomerates and encapsulated pigment agglomerates are particularly preferred.

The individual, luminescent, solid homogeneous phases forming the particulate agglomerates according to the invention can be based e.g. on an inorganic solid forming a matrix and doped with one or more rare earth metals or transition metals.

Suitable inorganic solids that are suitable for forming a matrix are for example:

oxides, in particular tri- and tetravalent oxides such as e.g. titanium oxide, aluminum oxide, iron oxide, boron oxide, yttrium oxide, cerium oxide, zirconium oxide, bismuth oxide, as well as more complex oxides such as e.g. garnets, including e.g. yttrium iron garnets, yttrium aluminum garnets, gadolinium gallium garnets;

perovskites, including yttrium aluminum perovskite, lanthanum gallium perovskite; spinels, including zinc aluminum spinels, magnesium aluminum spinels, manganese iron spinels; or mixed oxides such as e.g. ITO (indium tin oxide);

oxyhalides and oxychalcogenides, in particular oxychlorides such as e.g. yttrium oxychloride, lanthanum oxychloride; as well as oxysulfides, such as e.g. yttrium oxysulfide, gadolinium oxysulfide;

sulfides and other chalcogenides, e.g. zinc sulfide, cadmium sulfide, zinc selenide, cadmium selenide;

sulfates, in particular barium sulfate and strontium sulfate;

phosphates, in particular barium phosphate, strontium phosphate, calcium phosphate, yttrium phosphate, lanthanum phosphate, as well as more complex phosphate-based compounds such as e.g. apatites, including calcium hydroxyl apatites, calcium fluorapatites, calcium chlorapatites; or spodiosites, including e.g. calcium fluorospodiosites, calcium chlorospodiosites;

silicates and aluminosilicates, in particular zeolites such as e.g. zeolite A, zeolite Y; zeolite-related compounds such as e.g. sodalites; feldspars such as e.g. alkali feldspars, plagioclases;

further inorganic compound classes such as e.g. vanadates, germanates, arsenates, niobates, tantalates.

DETAILED DESCRIPTION OF VARIOUS EMBODIMENTS

The principle underlying the invention will be described in detail hereinafter in connection with FIGS. 1 to 4:

When safeguarding bank notes with security features on the basis of luminescent pigments (such as the above-mentioned inorganic matrices doped with rare earth metals or transition metals), it frequently suffices to incorporate a relatively small quantity of the feature. The mass fractions can lie in particular in the per mill range. When such a feature is incorporated into the paper of a bank note in a greatly diluted form, however, the spatial distribution of the pigment particles is not perfectly homogeneous under normal circumstances. With a purely random distribution of the pigment particles in the sheet pulp there are naturally regions with higher and lower particle concentrations. This can become apparent in intensity fluctuations upon measurement of the luminescence intensity at different places of the bank-note substrate.

It is known in the prior art to use encodings consisting of two or more luminescent substances as a security feature to increase security. Intensity fluctuations that are based on the random distribution of the pigment particles within the sheet pulp are independent of each other here. There is thus no relation between the random, location-dependent intensity fluctuations of two different feature substances. It is to be noted that this does not hold for inhomogeneities of the paper itself, e.g. in the case of locally different paper thicknesses. In this case, fluctuations of the luminescence intensity, e.g. low values at thinner places in the paper, would affect both feature substances to the same extent. Through a suitable choice of the security features and as low a concentration in the substrate as possible, substrate-induced fluctuations relative to the fluctuations induced by the random particle distribution can often be neglected (or be eliminated through suitable evaluation methods).

Figure 1:
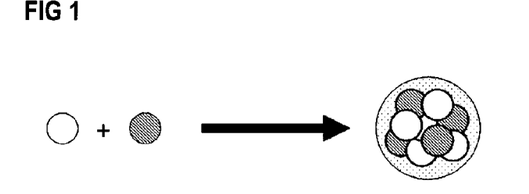
FIG. 1 shows two different luminescent substances are combined into a particulate agglomerate.

However, another picture results when two different luminescent substances are combined into a particulate agglomerate (see FIG. 1). For example, a particulate agglomerate that was obtained by agglomerating a mixture of the luminescent pigments "A" and "B" would unite both pigment types.

Figure 2:
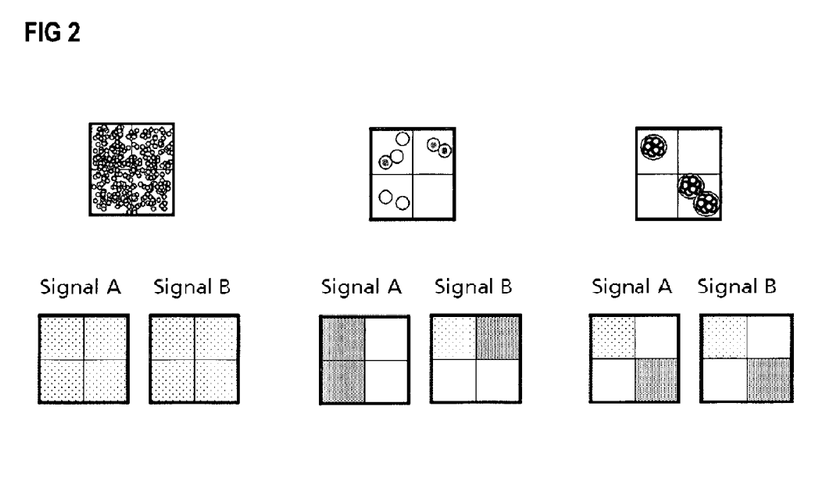
FIG. 2 shows a schematic comparison of luminescence intensities of luminous pigments "A" and "B" at four places in a paper substrate.
Figure 3:
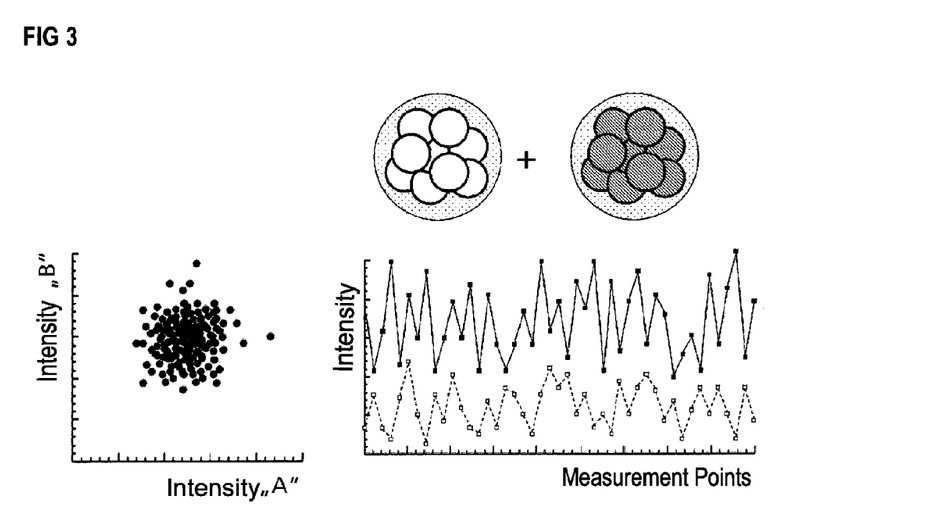
FIG. 3 shows signals of substances "A" and "B" fluctuating independently of each other inclusive of intensity and measurement points.

Upon the incorporation of a plurality of particulate agglomerates shown in FIG. 1 into paper and a random distribution in the paper pulp, a relation between the spatial distributions of the luminescent pigments "A" and "B" would arise independently of the substrate (see FIG. 2).

In FIG. 2, the luminescence intensities of the luminous pigments "A" and "B" are schematically compared at four places in a paper substrate, with the densely dotted areas symbolizing high signal intensities and the less densely dotted areas symbolizing less high signal intensities.

FIG. 2 left:

Pigments "A" and "B" respectively having a low luminescence intensity are used in high quantity. This leads to low fluctuations of the luminescence intensity in the individual regions. "Signal A" and "signal B" are always similarly strong.

FIG. 2 middle:

Pigments "A" and "B" respectively having a high luminescence intensity (which can be achieved e.g. by adjusting the particle size to larger particles, or by employing pure-substance agglomerates) are used in low quantity. This has the consequence that some regions yield a high "signal A" and some regions have a high "signal B". Between the two signals there is no relation, i.e. no statistical correlation. The term "pure-substance agglomerate" is understood to be an agglomerate having only particles of one particle type.

FIG. 2 right:

Particulate agglomerates that are obtainable from particles "A" and particles "B" are used. The starting substances A and B can respectively have a high or a low intensity. There result regions with elevated "signal A" and at the same time elevated "signal B", and regions with low "signal A" and at the same time low "signal B". In other words, there is a statistical correlation between the two signals.

The relation between "signal A" and "signal B" shown on the right in FIG. 2 is not necessarily directly proportional. The particulate agglomerates consist ideally, but not necessarily, of 50% particles A and 50% particles B. It is possible that a manufacturing method leads to particulate agglomerates with a statistical internal distribution of the pigments A and B. For example, there can arise agglomerate compositions that consist on average of ten pigment particles and include agglomerates with a composition "5A+5B", but also "3A+7B" and "7A+3B", etc. Thus, it is e.g. possible that at a measurement position on the paper substrate where a high local concentration of agglomerates is present, an especially strong signal of the luminescent substance "A" is measured but the signal of the luminescent substance "B" is not significantly elevated. However, this is unlikely, statistically speaking. If there is a local accumulation or depletion of the agglomerates one will likely find a accumulation or depletion of the signals of "A" and "B" to a certain degree. The signals thus correlate with each other. For further explanation of this correlation, there follows Application example 1:

Application Example 1:

Mixed agglomerates of two luminescent substances "A" and "B" were manufactured. For comparison, the agglomerates "only A" and the agglomerates "only B" were manufactured. Then a paper sheet with 2 wt. ‰ of the mixed agglomerates of "A" and "B" was prepared in a sheet former. Furthermore, a paper sheet with a mixture of 1 wt. ‰ "only A" and 1 wt. ‰ "only B" was prepared. Spectral examination yields that the signals of substance "A" and substance "B" are respectively recognizable in both sheets at the same wavelength and with comparable intensity. A conventional sensor checking e.g. the band position and luminescence intensity would thus ascertain no difference between the two sheets and recognize both as "identical" or "authentic". However, if the mutual correlation of the two signals of "A" and "B" is additionally heeded, clear differences can be seen between the sheets. For this purpose, the sheets were measured on a sensor that automatically checks the signal strength of the two features A and B simultaneously at several measurement positions. To increase the number of data points, a plurality of places on the sheet were measured and evaluated. In the case of the sheet with the two "pure" substances, the signals of "A" and "B" fluctuate independently of each other (see FIG. 3). When the intensities of "A" and "B" are plotted against each other graphically, a round point cloud hence arises. In the case of the sheet with the mixed agglomerates, a dependence of the signal fluctuations is recognizable (see FIG. 4). When the intensities of "A" and "B" are plotted against each other graphically, one recognizes a point distribution stretched along the axial diagonals. The point distribution indicates a correlation between the signal strength of the two components.

Figure 4:
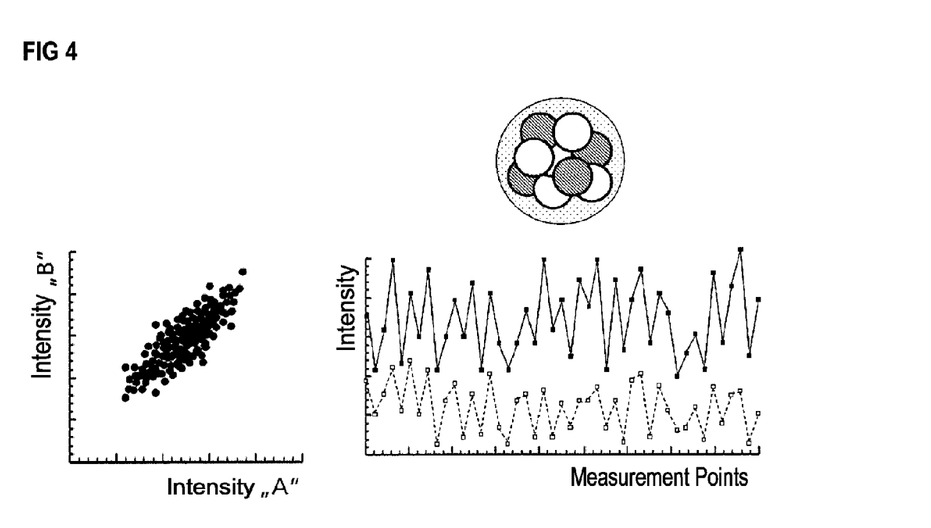
FIG. 4 shows signals of substances "A" and "B" as mixed agglomerates inclusive of intensity and measurement points.

If the normalized signal intensities of "A" and "B" were identical at all measurement positions of the paper substrate, the point distribution represented in FIG. 4 would ideally represent a line. This behavior is frequently not to be found in reality due to the statistical composition of the agglomerates, because for such a behavior all agglomerates would have to possess a fixed ratio of e.g. exactly 50% "A" fraction and exactly 50% "B" fraction. However, it is possible to produce such systems or an approximation to this condition in practice, e.g. by (1) an electrostatic preference of the heterogeneous agglomeration, or (2) a massive increase of the particle number per agglomerate, or (3) by employing nanoparticles, or (4) by controlled build-up of core-shell systems with defined sizes.

The evaluation of measuring data and determination of a statistical correlation will be described in detail hereinafter in connection with FIG. 5.

For the evaluation of measuring data and the determination of the presence or absence of a statistical correlation, different mathematical methods can be used.

Instead of "statistical correlation" one can also speak of a "statistical dependence". In this case it is checked whether pixel-wise a statistical dependence between the intensity "A" and the intensity "B" is present (yes/no decision).

There can in particular be defined quantitative measures which state how strong the pixel-wise statistical dependence between intensity "A" and intensity "B" is. In this manner, sorting classes can be defined.

There are numerous textbook methods for rating the strength of the dependence on random variables. The book, W. H. Press: "Numerical Recipes in C—The Art of Scientific Computing", Cambridge University Press, 1997, pages 628-645, whose disclosure is included herein by reference, describes e.g. the following methods:

Three data types: "nominal" (general classes, e.g. red, yellow); "ordinal" (ordered classes, e.g. good, medium, poor); "continuous" (continuous measurement values, e.g. 1.2, 3.5, 2.7). "Nominal" is the most general, "continuous" the most specific.

1. Continuous

Correlation, specifically linear correlation (correlation coefficient according to Bravais-Pearson). This type of calculation is suitable in particular with two-dimensional normal distributions. It is preferred to previously remove signal outliers from the statistics via quantiles.

2. Ordinal

Rank-order method: Carry out the calculations, not on the original values, but on the rank-order indices.

a) Spearman rank correlation coefficient: the above correlation coefficient according to Bravais-Pearson applied to the rank-order indices.

b) Kendall's tau: Examines how often the rank order is retained in all pairs of data points.

These methods are suitable for arbitrary distributions. In particular, signal outliers have no disturbing effect here.

3. Nominal

Evaluations based on contingency tables (i.e. tables with the absolute or relative frequencies of events with discrete (i.e. non-continuous) values).

a) Chi square evaluation for checking whether a statistical dependence is present.

b) Entropy-based evaluation. Example: Symmetric uncertainty coefficient.

Upon the application of these methods it is preferred to previously classify the two-dimensional real measurement values into two-dimensional classes via class intervals and to establish the two-dimensional frequencies (contingency table).

Further reading on the above topic: R. Storm: "Wahrscheinlichkeitsrechnung, mathematische Statistik and statistische Qualitätskontrolle", Carl Hanser Verlag, 12th edition, 2007, pages 246-285, whose disclosure is included herein by reference.

Further information on the above topic is obtainable on the Internet on the following pages:

http://en.wikipedia.org/wiki/Correlation_and_dependence http://en.wikipedia.org/wiki/Spearman %27s_rank_correlation_coefficient http://de.wikibooks.org/wiki/Mathematik:_Statistik:_Korrelationsanalyse http://de.wikipedia.org/wiki/Rangkorrelationskoeffizient For the sake of better comprehension, two statistical methods for evaluation will hereinafter be described by way of example.

Example 1

The Following Correlation Function $$Kor(X, Y) = \frac{\text{Cov}(X, Y)}{\sigma_X \cdot \sigma_Y} = \frac{\frac{1}{n}\sum_{i=1}^{n}(x_i - \mu_X) \cdot (y_i - \mu_Y)}{\sigma_X \cdot \sigma_Y}$$

It provides a positive contribution when two data points of a row are simultaneously located above or below their respective average, i.e. two "high" or two "low" signal intensities of "A" and "B" are respectively located at the same location.

Example 2

Figure 5:
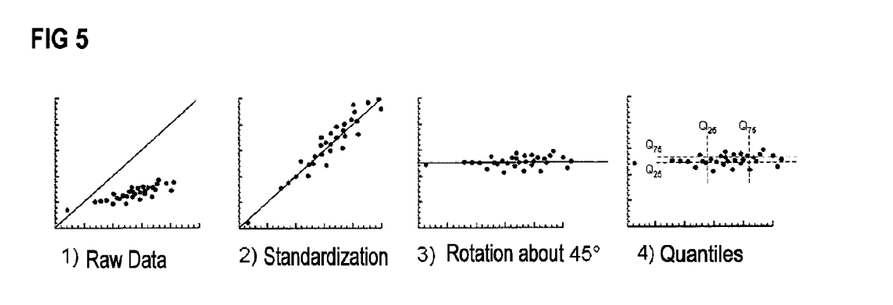
FIG. 5 shows evaluation of measuring data and determination of a statistical correlation.

Method having several steps, with the aim of evaluating the length-to-width ratio of the point clouds obtained from the measuring data (see FIG. 5). To minimize the influence of "outliers", 25% of the highest and lowest signal values were ignored, respectively. Correlating point clouds are elongated and possess a very pronounced length-to-width ratio, while non-correlating point clouds have a length and width that are about equally great.

The value document according to the invention can additionally have in the region of the luminescent encoding a print, a watermark and/or a security element on the basis of a security patch or of a security strip. Such additional security elements are factors that disturb the correct evaluation of the statistical correlation or cause an additional correlation effect that is not caused by the special build-up of the particulate agglomerate according to the invention. This includes all factors through which the signal strength of the two luminescences to be evaluated is changed at the same place in the paper substrate. This may be e.g. an attenuation or amplification which is to be ascribed to one of the following causes:

a local change of thickness or density in the paper substrate, e.g. in the case of a watermark;

an absorption of the excitation radiation for the luminescence feature through a print (or an overprinting) or a security strip;

an additional emission radiation which comes from a print (or an overprinting) or a security strip.

Figure 6:
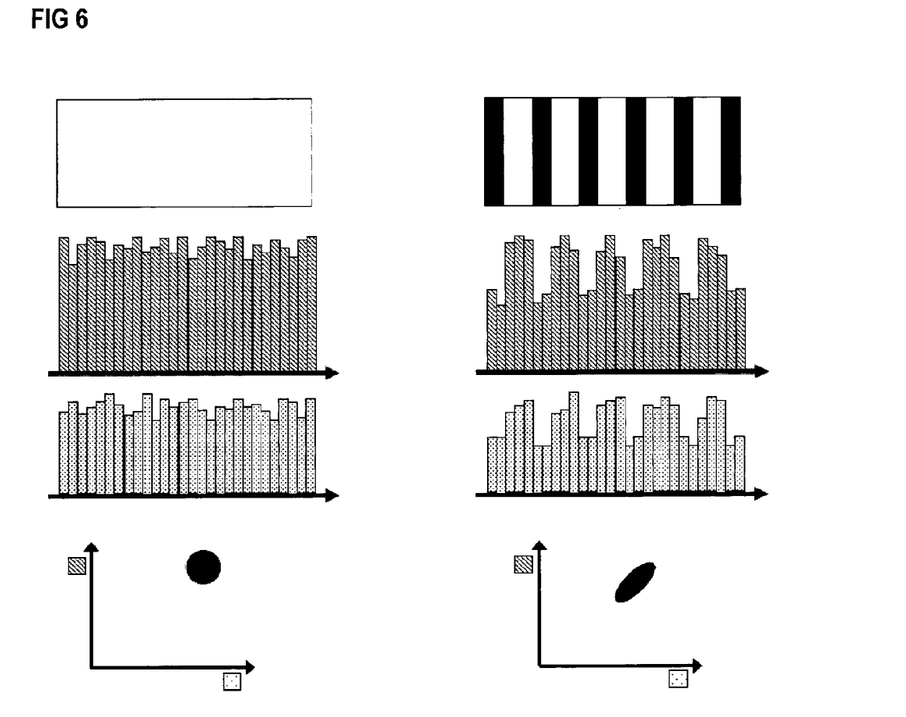
FIG. 6 shows a comparison between the luminescence signals of two non-correlating luminophores in an unprinted paper substrate and after overprinting with a stripe pattern.

FIG. 6 shows a comparison between the luminescence signals of two non-correlating luminophores in an unprinted paper substrate and after overprinting with a stripe pattern. In the unprinted paper substrate, as expected, there is no noticeable relation between the signal strengths of the two luminophores. After the overprinting, however, there is an attenuation of the signal at the overprinted places, which causes a spatial correlation of the signal intensities of the two luminophores. There thus arises a similar effect as is obtained by the use of the particulate agglomerates according to the invention. Consequently, it is difficult to distinguish clearly between "normal" features, i.e. ones not according to the invention, and features according to the invention. Two ways will hence be specified hereinafter by way of example for eliminating or reducing such unwanted correlation effects caused by overprinting or the like:

Correction Method 1:

There is introduced into the value document in uniform concentration an additional ("third") component luminescing at a third emission wavelength, said component being non-correlating. Introducing a suitable, third non-correlating luminescence component and normalization through its signal intensity cause e.g. all of the above-described spurious effects to vanish. Especially suitable luminescent substances here are those that have especially small, or ideally no, location-dependent fluctuations of luminescence intensity in an unmodified paper substrate, i.e. would possess a spatially homogeneous luminous intensity without additional influences. Applied to the example specified in FIG. 6, this would mean that the periodic attenuation by the overprinted stripe pattern accordingly influences not only the first two luminophores but also the third component. Since the extent of "attenuation" by external effects is known via the third homogeneous component, the initial states of all other components can be calculated back. This method thus eliminates all correlation effects that act on all three components equally, including overprinting and differences of thickness in the substrate, but has no influence on correlation effects that relate only to certain components. In this manner, there is no influence on the agglomeration-based correlation effects according to the invention.

Correction Method 2:

When it is undesirable to introduce the above-mentioned, third component e.g. for reasons of cost, other methods can also be used according to the case of application. When the luminescence intensity in an unmodified paper substrate is e.g. ordinarily above a certain threshold value and is only brought below this threshold value by overprinting effects or changes of thickness in the paper substrate, etc., corresponding data points can be eliminated from the analysis. This method is particularly suited for cases with abrupt and strong changes of intensity, e.g. in the case of an overprinting with sharply defined lines and regions, but less for gradual color gradations with smooth transitions or filigree patterns. When the measured regions lie close together locally it is advantageous, when the threshold value is undershot at one measurement point, to likewise eliminate all neighboring measurement points (see FIG. 7). This excludes partly overprinted measuring regions at the boundary of an overprinted region, even when their intensities lie above the threshold value due to the only incomplete overprinting.

Figure 7:
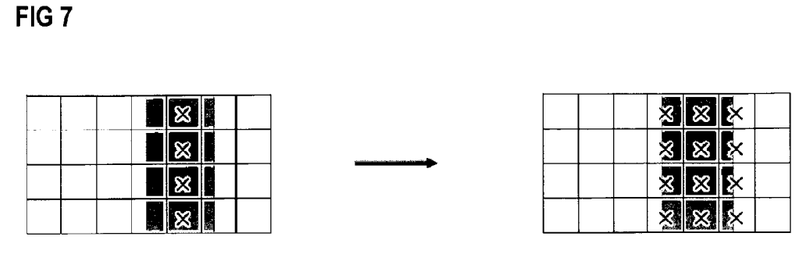
FIG. 7 shows how overprinted measuring regions below an intensity threshold value are excluded (designated with x's in the figure).

FIG. 7 shows how overprinted measuring regions below an intensity threshold value are excluded (designated with x's in the figure). Subsequently the neighboring regions are likewise excluded.

The particulate agglomerates according to the invention will be described hereinafter by preferred embodiments in connection with FIG. 8.

In principle, a number of manufacturing methods are suitable for producing the particulate agglomerates according to the invention starting out from two (or three) luminescent substances. Normally, the luminescence particles previously present in single form are caused to congregate into a greater unit. The thus obtained greater unit is subsequently so fixed that the particles can no longer separate from each other during application as a security feature. It is decisive here that the greater units include, as far as possible, equal parts of the two (or the three) luminescent substances, whereby most manufacturing methods yield a random statistical mixture of the particles.

A congregation of like particles is undesirable, so that the agglomerates only include a single luminophore type. This can be effected e.g. when the different luminophores are insufficiently intermixed before the congregation process, or the congregation of like-kind substances is promoted by surface effects or the like. However, such effects are negligible normally, or when the synthesis procedures are performed correctly.

An important factor is the sizes of the particles that build up the agglomerate, as well as the size of the arising agglomerate itself. For applications as a security feature in the bank-note sector, the agglomerates should not exceed a grain size of 20 μm. The particles of which the agglomerate is composed should be considerably smaller, since with decreasing size a higher number of particles per agglomerate can be incorporated. A higher number of incorporated particles in turn increases the probability of finding a "suitable distribution" of the two particle types in the agglomerate.

The following relation is meant here: If the starting substance were so great that only three respective particles of the substances A and B could form an agglomerate without exceeding the maximum agglomerate size, the combinations 'AAA'/'AAB'/'ABB'/'BBB' would be conceivable. However, such a composition would be completely unsuitable for the use according to the invention. For 25% of the agglomerates would only consist of a single substance (AAA or BBB) and thus not produce a correlation, while one third of the other 75% would be one substance and two thirds thereof the second substance, thus producing only poor correlation values.

Imagining the opposite extreme case of an agglomerate built up from 10000 (or "infinitely many") single particles, the probability of all particles accidentally being identical is arbitrarily small. When equal quantities of the two particle types are used for synthesis, the mixing ratio in the agglomerates manufactured therefrom will also amount to 50% or hardly deviate therefrom. Such agglomerates would thus be well suited for use as the feature according to the invention.

In practice, one is frequently somewhere between these two extremes. The reduction of luminophore size usually leads to a noticeable loss of luminous intensity. Particularly as of a grain size of approx. 1 μm, many illuminants show a clear intensity loss, which is usually to be ascribed to the increase of the surface, since energy can be dissipated non-radiatively on surface defects here. An excessive grain size, however, leads to the above-described problems in the manufacture of suitable agglomerates.

As luminescent substances for building up the agglomerates, it is hence preferable to use small to medium-sized particles, e.g. with a grain size between 1 and 5 μm.

It should be mentioned, however, that if suitably intensive illuminants with a small particle size, e.g. in the nanometer range, are available, these could likewise be used.

The quantity ratio of the two substances A and B from which the agglomerates are manufactured amounts ideally to 1:1, if the two substances possess the same intensity and grain size. In the case of application it may be advantageous to adapt this ratio, e.g. if there are great differences in luminosity or different grain-size distributions. It may likewise be necessary in some cases to adapt the quantity ratio in order e.g. to produce a certain desired average intensity ratio of the two signals in the end product.

All previous descriptions relate for simplicity's sake to the production of agglomerates from two illuminants but, analogously, three or an arbitrary number of illuminants can also be united into an agglomerate, with the signal intensities of all illuminants involved thus correlating with each other.

The units designated "agglomerates" that respectively include a plurality of luminophore units are, according to one variant, a disordered heap of mutually adherent particles which have been fixed or permanently "stuck together" (see FIGS. 8a and b). This can be done e.g. by encasing with a polymer layer or silica layer (see e.g. WO 2006/072380 A2), or by linking the particle surfaces with each other via chemical groups, etc. Such agglomerates are relatively easy to manufacture technically and are hence preferred. According to a further variant, the particles can have another build-up without losing functionality (see FIGS. 8c, d and e). In some cases, alternative embodiments, such as ordered agglomerates or core-shell systems, can possess advantageous properties (e.g. a controlled particle distribution). However, their synthesis is usually more elaborate.

Figure 8:
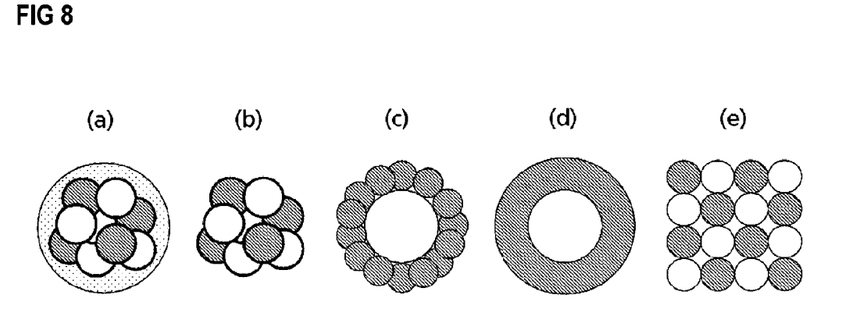
FIG. 8 shows the following examples with reference to the particulate agglomerates.

FIG. 8 shows the following examples with reference to the particulate agglomerates:

(a) disordered pigment agglomerate having two different (in particular mutually adherent) luminescent pigments and being encased or encapsulated with a polymer layer or silica layer;

(b) disordered pigment agglomerate having two different, mutually adherent luminescent pigments;

(c) core-shell particles in which the core is formed by a first luminescent pigment and the shell is formed by a plurality of second luminescent pigments;

(d) core-shell particles in which the core is formed by a first luminescent pigment and the continuous, homogeneous shell is formed of a second luminescent material;

(e) ordered pigment agglomerate having two different luminescent pigments.

For the above example of a disordered agglomerate, an example of synthesis will be described hereinafter:

For this purpose, the luminophores (or luminescent pigments) to be agglomerated are dispersed in water. A high concentration of dissolved potassium hydrogencarbonate leads to a temporary agglomeration of the luminophore particles (the repulsive surface charge being shielded by potassium cations). The average agglomerate size can be adjusted by controlling the stirring rate, temperature, concentration, etc. It is important here to allow no, or next to no, shear forces to arise, since they would otherwise split the agglomerates into single particles again. The agglomerated state is fixed by slow metered addition of potassium water glass, since the latter reacts with the dissolved hydrogencarbonate to form silica and thus coats the agglomerate or "sticks together" the individual particles. After filtration, the product can be tempered at 250° C. to additionally strengthen the cohesion of the particles contained in the agglomerate.

Further exemplary embodiments as well as advantages of the invention will be explained hereinafter in connection with FIGS. 9-12.

NIR Luminescent Pigments

The abbreviation "NIR" designates the term "near infrared".

The application examples employ five inorganic NIR luminescent pigments with the following properties:

NIR luminescent pigment "A": Luminescence maximum 1000 nm upon excitation at 802 nm;

NIR luminescent pigment "B": Luminescence maximum 1082 nm upon excitation at 802 nm;

NIR luminescent pigment "C": Luminescence maximum 1545 nm upon excitation at 950 nm;

NIR luminescent pigment "D": Luminescence maximum 2040 nm upon excitation at 950 nm;

NIR luminescent pigment "E": Luminescence maximum 1792 nm upon excitation at 950 nm;

All pigments have a grain size of D99<5 μm and D50<2 μm

Formula 1 for Producing a Luminescence-Particle Agglomerate 10 g NIR luminescent pigment is dispersed in 60 g water. There are added 120 ml ethanol and 3.5 ml ammonia (25%). While stirring, 10 ml tetraethyl orthosilicate is added and the reaction mixture stirred for eight more hours. The product is filtered off, washed with 40 ml water twice and dried in the drying oven at 60° C. Particle agglomerates with a grain size D99=20-30 μm are obtained. The obtained agglomerates are tempered for one hour at 300° C. and subsequently treated with an ultra centrifugal mill. There is obtained a product with a reduced grain size D99=15-18 μm.

Formula 2 for Producing a Luminescence-Particle Agglomerate 33 g NIR luminescent pigment is dispersed in 245 g water. There are added 44 g potassium hydrogencarbonate and, while stirring, a potassium water glass solution added in drops over the course of one hour, so that a $SiO_2$ fraction of approx. 20% is present in the product at the end. The product is filtered off, washed with 150 ml water twice and dried in the drying oven at 60° C. There are obtained particle agglomerates with a grain size D99=18-20 μm Produced Agglomerates "AB1": 5 g NIR pigment A and 5 g NIR pigment B are treated according to Formula "A1": 10 g NIR pigment A is treated according to Formula 1.

"B1": 10 g NIR pigment B is treated according to Formula 1.

"CD2": 16.6 g NIR pigment C and 16.6 NIR pigment D are treated according to Formula 2.

"C2": 33 g NIR pigment C is treated according to Formula 2.

"D2": 33 g NIR pigment D is treated according to Formula 2.

Application Example 1: Signal Correlation in the Paper Substrate without Correction Component The agglomerates (AB1) having two luminescent pigments are so added to the paper pulp during sheet production that the agglomerates AB1 are distributed in the paper body homogeneously with a mass fraction of 0.1 percent by weight in the arising sheet. The sheet is subsequently measured at a plurality of different places by excitation with light of the wavelength 802 nm (size of measurement spot about 1 $mm^2$). The intensities of the luminescence are respectively detected at 1000 nm (A) and 1082 nm (B). Plotting the obtained measurement points yields the graph in FIG. 9.

Figure 9:
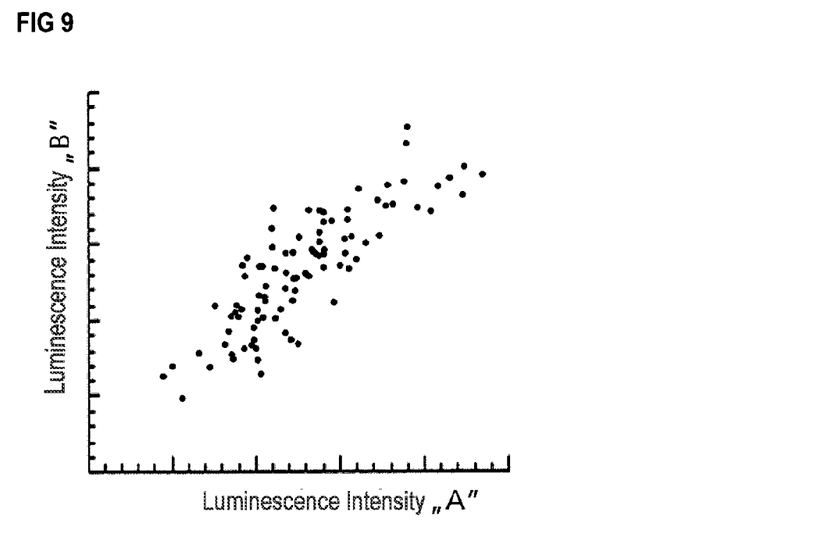
FIG. 9 shows the relative luminescence intensities at 1000 nm (A) (y-axis) and 1082 nm (B) (x-axis) at different places in the paper substrate with agglomerates AB1 built up from two luminescent pigments.

FIG. 9 shows the relative luminescence intensities at 1000 nm (A) (y-axis) and 1082 nm (B) (x-axis) at different places in the paper substrate with agglomerates AB1 built up from two luminescent pigments.

As a comparative example there is manufactured a second sheet which contains 0.05 percent by weight agglomerates A1 consisting of the pure pigment A, and 0.05 percent by weight agglomerates B1 consisting of the pure pigment B, and it is likewise measured. Plotting the obtained measurement points yields the graph in FIG. 10.

Figure 10:
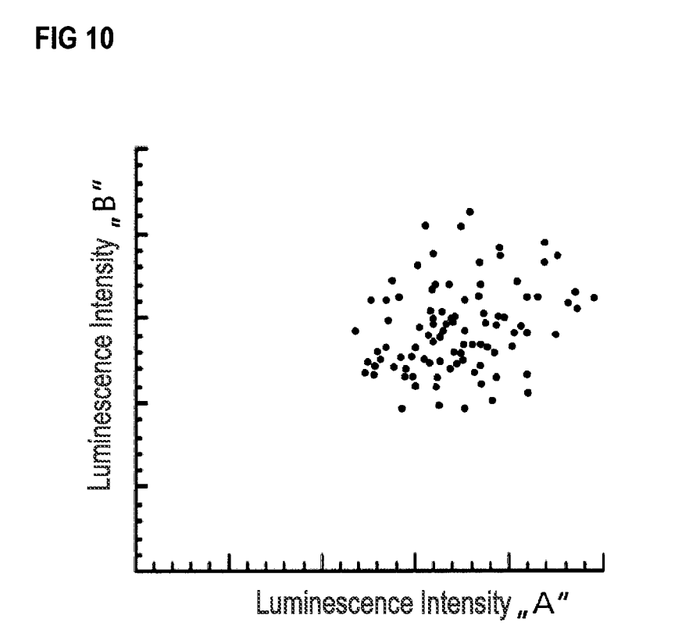
FIG. 10 shows the relative luminescence intensities at 1000 nm (A) (x-axis) and 1082 nm (B) (y-axis) at different places in the paper substrate with agglomerates A1 and B1 respectively built up from one sort of luminescent pigment.

FIG. 10 shows the relative luminescence intensities at 1000 nm (A) (x-axis) and 1082 nm (B) (y-axis) at different places in the paper substrate with agglomerates A1 and B1 respectively built up from one sort of luminescent pigment.

Calculating for example the correlation coefficient of the data points from FIG. 9, one obtains a high correlation value of 73%. However, the data points from FIG. 10 correlate considerably more weakly, there is obtained a correlation coefficient of 30%.

When performing a series of 100 measurements which are done on the sheets at random places, one typically obtains correlation values of over 70% for the sheet containing agglomerates AB1 composed of two pigments. For the sheet containing the agglomerates (A1, B1) built up respectively with one sort of luminescent pigment, there are obtained considerably lower values, in particular under 50%.

The sheets can thus be distinguished by the degree of correlation, although they contain equal weight fractions of the two NIR luminescent pigments A and B.

The fact that a correlation is recognizable at all in the second case is to be ascribed primarily to inhomogeneities of the paper, which increase or lower the luminescence intensity at a measuring location respectively for both components A and B simultaneously. The inhomogeneities of the paper are dependent, inter alia, on the paper type and the manufacturing method.

Preferably, the method described in the following Application example 2 for correcting printing effects by an additional luminescence component is also chosen in the case of unprinted paper.

Application Example 2: Signal Correlation in a Printed Sheet with Correction Component The agglomerates (CD2) having two luminescent pigments, and the additional component E (not agglomerated) are so added to the paper pulp during sheet production that the agglomerates CD2 are distributed in the paper body homogeneously with a mass fraction of 0.2 percent by weight, as well as the component E with a mass fraction of 0.5 percent by weight, in the arising sheet. Subsequently the sheet is printed with a black stripe pattern (stripe thickness approx. 1 cm), thereby obtaining a significant luminescence attenuation (to approx. 50% of the original signal) at the printed places.

For comparison there is manufactured an analogous sheet with 0.1 percent by weight of the agglomerates C2 and D2, respectively, and 0.5 percent by weight of the additional component E, and it is likewise printed.

Both sheets are measured at a plurality of different places by excitation with light of the wavelength 950 nm (size of measurement spot about 0.8 $mm^2$). The intensities of the luminescence are respectively detected at 1545 nm (C), 2040 nm (D) and 1792 nm (E).

Figure 11:
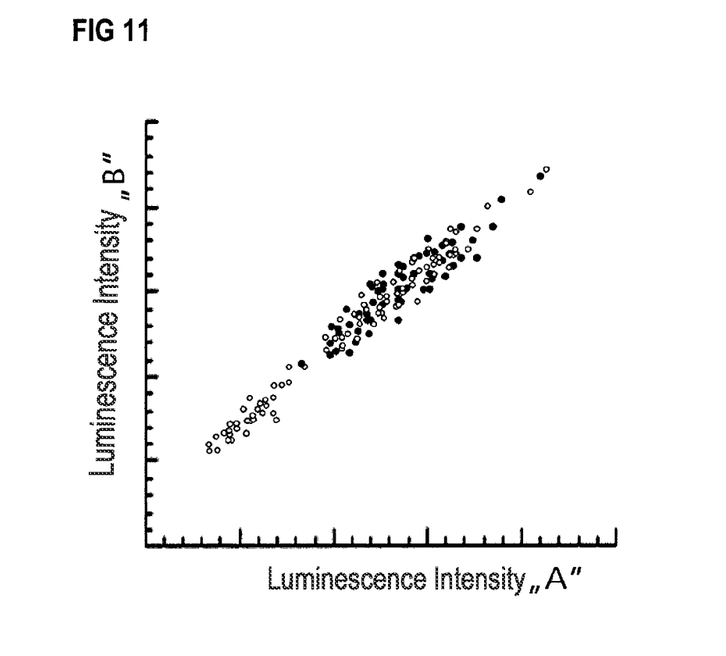
FIG. 11 shows the relative luminescence intensities at 1545 nm (C) (x-axis) and 2040 nm (D) (y-axis) at different places in the paper substrate with agglomerates CD2 built up from two luminescent pigments before (white) and after (black) correction through the luminescence intensity at 1792 nm (E) of an additional luminescent pigment.
Figure 12:
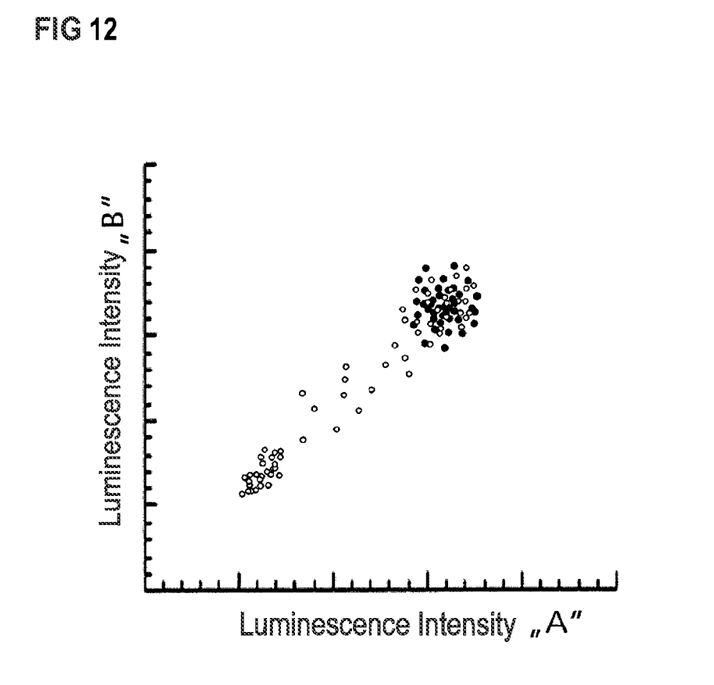
FIG. 12 shows the relative luminescence intensities at 1545 nm (C) (x-axis) and 2040 nm (D) (y-axis) at different places in the paper substrate with agglomerates C2 and D2 built up respectively from one sort of luminescent pigment before (white) and after (black) correction through the luminescence intensity at 1792 nm (E) of an additional luminescent pigment.

Through the local attenuation of the detected luminescence intensity in the printed regions, both the sheet with the agglomerates CD2 and the sheet with the agglomerates C2 and D2 show a strong correlation of the signal intensities C and D (white points in FIG. 11 and FIG. 12).

FIG. 11 shows the relative luminescence intensities at 1545 to nm (C) (x-axis) and 2040 nm (D) (y-axis) at different places in a paper substrate with agglomerates CD2 built up from two luminescent pigments before (white) and after (black) correction through the luminescence intensity at 1792 nm (E) of an additional luminescent pigment.

FIG. 12 shows the relative luminescence intensities at 1545 nm (C) (x-axis) and 2040 nm (D) (y-axis) at different places in a paper substrate with agglomerates C2 and D2 built up respectively from one sort of a luminescent pigment before (white) and after (black) correction through the luminescence intensity at 1792 nm (E) of an additional luminescent pigment.

Since the effect of the printing, just like the effect of the inhomogeneities of the paper pulp, affects all three components C, D, E equally, these effects can be eliminated by normalization of the signal intensities C, D by the signal intensity E (black points in FIG. 11 and FIG. 12). As a result, a correlation can only be ascertained in the sheet with the agglomerates CD2, while no correlation can be ascertained any longer in the sheet with the separate components C2 and D2.

Thus, after performing a series of 100 measurements, which are done at random places in the paper substrate, the correlation coefficient amounts to 0.97 in the sheet with agglomerates CD2 before correction, and 0.87 after correction. A strong correlation thus still prevails between C and D, whereas the sheet with agglomerates C2 and D2 has a value of 0.97 before correction and a low value of 0.12 after correction.

The luminescent encoding pattern described in the present invention is not restricted to a bar-code system or an encoding grid as is represented e.g. in FIG. 2 and FIG. 7. The "grids" shown in the figures were chosen arbitrarily, i.e. the measuring locations can be selected arbitrarily with respect to their size and position and need not lie within such a grid.

In principle, the luminescent substances employed according to the invention can be incorporated in the value document itself, in particular in the paper substrate. Additionally or alternatively, the luminescent substances can be applied on the value document (e.g. the luminescent substances can be imprinted on the paper substrate). The value-document substrate need not necessarily be a paper substrate, but might also be a plastic substrate or a substrate having both paper constituents and plastic constituents.

The invention claimed is:

1. A value document having luminescent, particulate agglomerates which respectively include at least two different, luminescent, solid homogeneous phases emitting at a first and a second emission wavelength, respectively, wherein upon an evaluation of measurement values that are obtainable by a measurement of the first luminescence intensity at the first emission wavelength and of the second luminescence intensity at the second emission wavelength, said measurement being location-specific and carried out at different locations of the value document, a statistical correlation is present between the first luminescence intensities and the second luminescence intensities.

2. The value document according to claim 1, wherein the luminescence intensities used for the evaluation are, respectively, corrected measurement values converted by means of an algorithm.

3. The value document according to claim 1, wherein the agglomerates are chosen from the group consisting of core-shell particles, pigment agglomerates, encapsulated pigment agglomerates and pigments encased by nanopigments.

4. The value document according to claim 1, wherein the particulate agglomerates have a grain size D99 in a range of 1 micrometer to 30 micrometers.

5. The value document according to claim 1, wherein the particulate agglomerates have a grain size D50 in a range of 1 micrometer to 30 micrometers.

6. A method for checking the presence of a value document according to claim 1 which comprises the following steps:
   a) exciting the luminescent substances to emission;
   b) capturing measurement values in a location-resolved and wavelength-selective manner for the radiation emitted by the luminescent substances, there being produced for each of the first and the second emission wavelength measurement-value pairs involving emission wavelength and location, to thereby obtain first luminescence intensities at the first emission wavelength and second luminescence intensities at the second emission wavelength;
   c) checking whether a statistical correlation is present between the first luminescence intensities and the second luminescence intensities.

7. A value-document system having at least first value documents and second value documents, wherein the first value documents are respectively chosen according to claim 1 and the first value documents are distinguishable from the second value documents by the statistical correlation of their luminescence intensities.

8. The value-document system according to claim 7, wherein the second value documents have no statistical correlation.

9. The value-document system according to claim 7 having first value documents, second value documents, third value documents and fourth value documents, of which the third value documents and the fourth value documents are only optional, namely:
   a) first value documents which respectively have a luminescent mixture consisting of luminescent, particulate agglomerates (A+B) and luminescent particles C, wherein
   the particulate agglomerates (A+B) respectively include two different, luminescent, solid homogeneous phases A and B emitting at a first and a second emission wavelength, respectively, and the luminescent particles C respectively consist of a solid homogeneous phase C emitting at a third emission wavelength, and
   upon an evaluation of measurement values that are obtainable by a measurement of the first luminescence intensity at the first emission wavelength, of the second luminescence intensity at the second emission wavelength and of the third luminescence intensity at the third emission wavelength, said measurement being location-specific and carried out at different locations of an individual value document, a statistical correlation is present only between the first luminescence intensities and the second luminescence intensities;
   b) second value documents which respectively have a luminescent mixture consisting of luminescent, particulate agglomerates (B+C) and luminescent particles A, wherein
   the particulate agglomerates (B+C) respectively include the two different, luminescent, solid homogeneous phases B and C emitting at the second and the third emission wavelength, respectively, and the luminescent particles A respectively consist of the solid homogeneous phase A emitting at the first emission wavelength, and
   upon an evaluation of measurement values that are obtainable by a measurement of the first luminescence intensity at the first emission wavelength, of the second luminescence intensity at the second emission wavelength and of the third luminescence intensity at the third emission wavelength, said measurement being location-specific and carried out at different locations of an individual value document, a statistical correlation is present only between the second luminescence intensities and the third luminescence intensities;
   optionally c) third value documents which respectively have a luminescent mixture consisting of luminescent, particulate agglomerates (A+C) and luminescent particles B, wherein
   the particulate agglomerates (A+C) respectively include the two different, luminescent, solid homogeneous phases A and C emitting at the first and the third emission wavelength, respectively, and the luminescent particles B respectively consist of the solid homogeneous phase B emitting at the second emission wavelength, and
   upon an evaluation of measurement values that are obtainable by a measurement of the first luminescence intensity at the first emission wavelength, of the second luminescence intensity at the second emission wavelength and of the third luminescence intensity at the third emission wavelength, said measurement being location-specific and carried out at different locations of an individual value document, a statistical correlation is present only between the first luminescence intensities and the third luminescence intensities; and optionally d) fourth value documents which respectively have luminescent, particulate agglomerates (A+B+C), wherein the particulate agglomerates (A+B+C) respectively include the three different, luminescent, solid homogeneous phases A, B and C emitting at the first and the second and the third emission wavelength, respectively, and upon an evaluation of measurement values that are obtainable by a measurement of the first luminescence intensity at the first emission wavelength, of the second luminescence intensity at the second emission wavelength and of the third luminescence intensity at the third emission wavelength, said measurement being location-specific and carried out at different locations of an individual value document, a statistical correlation is present between the first luminescence intensities, the second luminescence intensities and the third luminescence intensities.

* * * * *